United States Patent
Eklin

(10) Patent No.: US 7,426,019 B2
(45) Date of Patent: Sep. 16, 2008

(54) METHOD AND ARRANGEMENT FOR NON-DESTRUCTIVE COMPOSITION ANALYSIS OF DELICATE SAMPLES

(75) Inventor: Tero Eklin, Espoo (FI)

(73) Assignee: Oxford Instruments Analytical Oy (FI)

( * ) Notice: Subject to any disclaimer, the term of this patent is extended or adjusted under 35 U.S.C. 154(b) by 165 days.

(21) Appl. No.: 11/417,689

(22) Filed: May 4, 2006

(65) Prior Publication Data

US 2006/0262302 A1    Nov. 23, 2006

(30) Foreign Application Priority Data

May 4, 2005    (EP)    ................................. 05103746

(51) Int. Cl.
*G01N 21/00*    (2006.01)
(52) U.S. Cl. ..................... 356/30; 356/237.1
(58) Field of Classification Search ................... 356/30, 356/425, 432, 461, 300–324, 237.1–237.6, 356/239.1–239.8; 250/226, 341.1
See application file for complete search history.

(56) References Cited

U.S. PATENT DOCUMENTS 4,191,475 A    3/1980    Sourrouille

| | | |
|---|---|---|
| 4,645,342 A | 2/1987 | Tanimoto et al. |
| 5,583,634 A | 12/1996 | Andre et al. |
| 5,793,485 A * | 8/1998 | Gourley ...................... 356/318 |
| 6,008,896 A | 12/1999 | Sabsabi et al. |
| 2001/0036243 A1 | 11/2001 | Niemax et al. |
| 2002/0159059 A1* | 10/2002 | Sabsabi et al. ............. 356/318 |
| 2003/0155513 A1* | 8/2003 | Remillard et al. ......... 250/341.8 |
| 2003/0218747 A1 | 11/2003 | Ramaseder et al. |
| 2004/0012780 A1* | 1/2004 | Sharma ...................... 356/318 |
| 2004/0125371 A1* | 7/2004 | Chang et al. ................. 356/318 |

FOREIGN PATENT DOCUMENTS

| DE | 103 04 337 A1 | 8/2004 |
|---|---|---|
| WO | WO 00/20847 | 4/2000 |
| WO | WO 01/33202 A1 | 5/2001 |

\* cited by examiner

*Primary Examiner*—Gregory J. Toatley, Jr.
*Assistant Examiner*—Tri T Ton
(74) *Attorney, Agent, or Firm*—Wood, Phillips, Katz, Clark & Mortimer

(57) ABSTRACT

An arrangement and a method are provided for non-destructively analyzing the composition of a delicate sample. The value of the sample depends at least partly on absence of visual defects. A laser source (301) produces a pulsed laser beam, and focusing optics (302) focus said pulsed laser beam into a focal spot on the sample. A sensor (312) receives and detects optical emissions from particles of the sample excited by said pulsed laser beam. A processing subsystem (111) produces information of the composition of the sample based on the optical emissions detected by said sensor (312).

23 Claims, 3 Drawing Sheets

METHOD AND ARRANGEMENT FOR NON-DESTRUCTIVE COMPOSITION ANALYSIS OF DELICATE SAMPLES

TECHNICAL FIELD

The present invention concerns the technical field of non-destructively analyzing the composition of delicate samples. Non-destructive analysis means here that the analysis does not leave marks or traces on the sample that would be visible to the human eye, or otherwise noticeable by a human user without technical equipment. A delicate sample is one the value of which would be significantly reduced if such marks or traces would appear. As an example of delicate samples we will consider pieces of precious metals and precious stones, such as jewellery or separate gemstones.

BACKGROUND OF THE INVENTION

The value of a jewel or ornament made of precious metal depends at least partly on its material composition. It is not unusual to alloy cheaper materials with e.g. gold, and still sell the final product at a price that would only be justified if the material was solid gold. Another commonly used trick is plating an object made of cheaper materials with a thin layer of gold or other precious metal. Pricing might be more transparent if a cheap, simple and reliable way was available for determining the material composition of such a sample. Non-destructiveness is a strict prerequisite in such applications, because not only the material composition but also the visual appearance and integrity of the sample typically plays a major role in determining its value.

Non-destructive composition analysis of jewels and other corresponding delicate samples has also other applications than preventing cheating. Gemstones having a common geological origin carry a "fingerprint" of their origin in their composition. Minor traces of impurities tend to appear in similar mutual relations in gemstones coming from the same mine. By analyzing the material composition it is possible to deduce, from which source does a sample come from, which has important applications in e.g. tracking stolen or other illegally transported jewellery.

Microanalysis is closely related to non-destructive analysis of delicate samples, because microanalysis means analyzing the material composition of sample objects that are so small and/or so few that they must be treated very carefully. Microanalysis is needed for example in crime scene investigation to trace the origin of fibers, paint flakes or other small pieces of evidence. Other applications of microanalysis include, without being limited to, quality control of industrial processes, determining the contents of inclusions in geology, and tracking the origins of impurities in semiconductors.

Traditional methods of composition analysis have been chemical. A small chip of a metal jewel has been cut off and subjected to interaction with various chemical compounds under microscope. A drawback of such methods is that they are not completely non-destructive: the chip has to be taken from a place where the cutting trace will be least visible. Additionally chemical analysis is relatively slow and may require the use of strong acids and other hazardous substances.

Microanalysis has traditionally required the use of vacuum chambers, electron beams and other kinds of complicated technical equipment, which dictates that it has only been feasible for use in a sophisticated laboratory environment.

Other known composition analysis methods are X-ray fluorescence analysis and optical emission spectroscopy. Of these, in the former it is difficult to achieve the required energy resolution; for example the K-alpha line of copper and the K-beta line of zinc are so close to each other that these two important alloying metals are difficult to separate from each other. Optical emission spectroscopy requires a part of the sample substance to be heated to a state of plasma, which has traditionally been achieved by igniting an electric spark between the sample surface and an electrode in the measurement apparatus. The electric discharge and local heating eat into the material surface so badly that a very clearly visible crater is produced, which means that the method is far from non-destructive.

SUMMARY OF THE INVENTION

An objective of the present invention is to present an arrangement and a method for non-destructively determining the material composition of delicate targets. The apparatus should be reliable, simple to use and feasible for operation under field conditions.

The objectives of the invention are achieved by using laser-induced breakdown spectroscopy.

An arrangement according to the invention is meant for non-destructively analyzing the composition of a delicate sample, a value of which depends at least partly on absence of visual defects. It comprises:
- a laser source adapted to produce a pulsed laser beam,
- focusing optics adapted to focus said pulsed laser beam into a focal spot on the sample,
- a sensor adapted to receive and detect optical emissions from particles of the sample excited by said pulsed laser beam and
- a processing subsystem adapted to produce information of the composition of the sample based on the optical emissions detected by said sensor.

A method according to the invention is meant for non-destructively analyzing the composition of a delicate sample, a value of which depends at least partly on absence of visual defects. It comprises:
- producing a pulsed laser beam and focusing said pulsed laser beam into a focal spot on a surface of said sample,
- detecting optical emissions coming from particles of said sample upon said sample being exposed to said pulsed laser beam at said focal spot and
- determining the material composition of said sample based on the detected optical emissions.

A so-called passively Q-switched laser is a laser source in which a pump beam stores optical energy into a suitably doped crystal, one end of which comprises a saturable absorber. When the saturation limit of the absorber has been reached, the optical energy gushes out from the crystal in a very short pulse. By suitably focusing the resulting pulsed laser beam it is possible to achieve a remarkable energy density within a focal spot of micrometer or even sub-micrometer scale diameter for the duration of some nanoseconds. The energy density is high enough to change a very small portion of the sample into plasma, which produces optical emissions. By analyzing the spectrum of these optical emissions it is possible to determine the material composition of the plasma plume. The optical spectra of both noble metals and the most common alloying materials are so simple that it is easy to differentiate between them.

Since the diameter of the focal spot and consequently the area from which sample material was taken is so small, the method leaves no visual trace on the surface. On the other hand the energy density is so high that in case the pulsed laser is kept focused onto the same spot, it produces a so-called drilling effect, which means that it penetrates deeper and deeper into the sample material, to depths that are meaningful in detecting e.g. plating layers made of noble metals. If such microscopic drilling of the sample surface is not wanted, it is possible to sweep the focal spot across the sample surface during the measurement. This way also a more representative portion of the sample is subjected to the measurement.

The high energy density further means that the method is applicable for analyzing the material composition of even substances with high optical transmittance, such as glass or even diamond.

The exemplary embodiments of the invention presented in this document are not to be interpreted to pose limitations to the applicability of the appended claims. The verb "to comprise" is used in this document as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific embodiments when read in connection with the accompanying drawings.

DETAILED DESCRIPTION OF THE INVENTION

Figure 1:
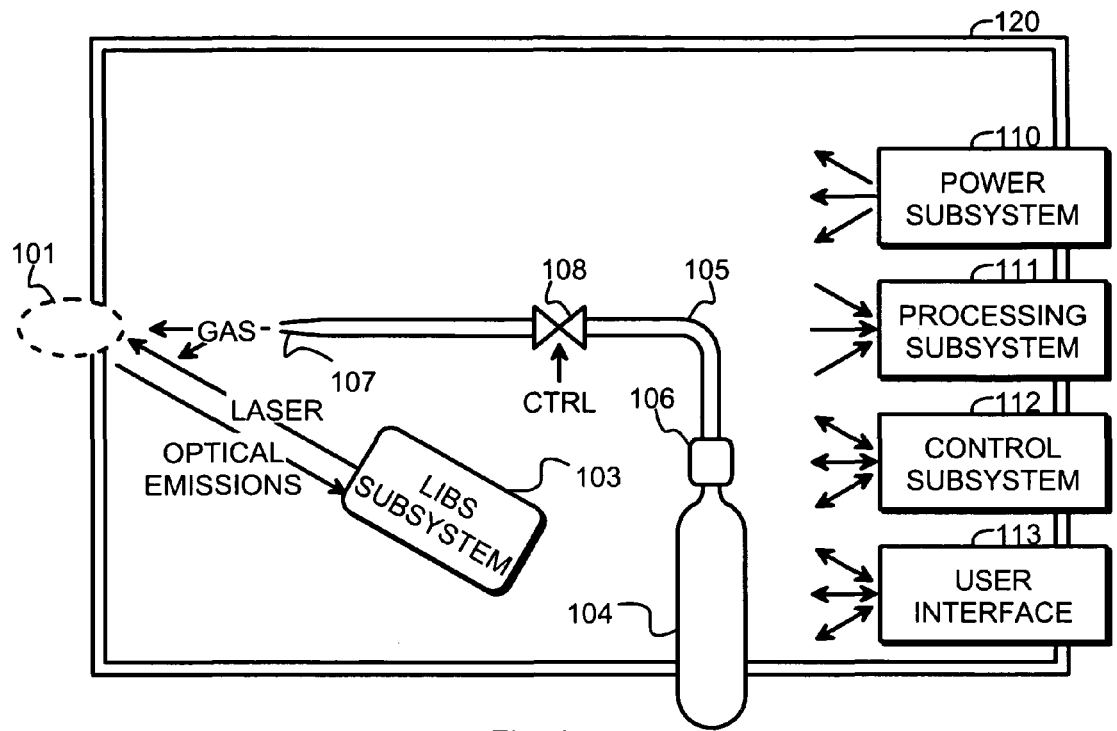
FIG. 1 illustrates a measurement apparatus according to an embodiment of the invention.

FIG. 1 is a schematic block diagram of a measurement apparatus according to an embodiment of the invention. The measurement apparatus is meant for analyzing the material composition of a sample located within a sample area 101. A laser-induced breakdown spectroscopy subsystem 103 (also designated as the LIBS subsystem for short) is provided for focusing a powerful laser beam onto a surface of the sample and for collecting and detecting optical emissions coming from a plasma plume created by said laser beam.

It is possible to perform laser-induced breakdown spectroscopy in ambient air, but the chemical stability of the plasma can be enhanced and the optical emission performance of many substances can be greatly enhanced by using a local protective gas atmosphere. In order to controllably create a local gas atmosphere around the location where the measurement is taking place, the apparatus of FIG. 1 comprises a gas administration subsystem, which is shown to comprise a gas cylinder 104, a gas conduit 105 and attachment means 106 for attaching the gas cylinder 104 to one end of the gas conduit 105. At the other end of the gas conduit 105 there is a nozzle 107, and a controllable valve 108 is provided for controlling the flow of gas from the gas cylinder 104 through the gas conduit 105 and the nozzle 107 towards the sample area 101. Additionally or alternatively the nozzle 107 may be adapted to direct the gas from the gas conduit 105 to the optical path between the sample area 101 and the LIBS subsystem 103.

Other parts of the measurement apparatus include a power subsystem 110 adapted to provide all other parts with the required operating power, a processing subsystem 111 adapted to receive information about detected optical emissions from the LIBS subsystem 103, a control subsystem 112 adapted to control the operation of all controllable parts of the apparatus, as well as a user interface 113 adapted to provide the user with information about the measurement results and overall operation of the apparatus and for offering the user some means for giving inputs. The provision of further functionalities is not excluded; for example a measurement apparatus of this kind typically includes a data exchange connection for coupling it to external computer devices. An outer cover 120 encloses at least a major portion of the other parts shown in FIG. 1.

Figure 2:
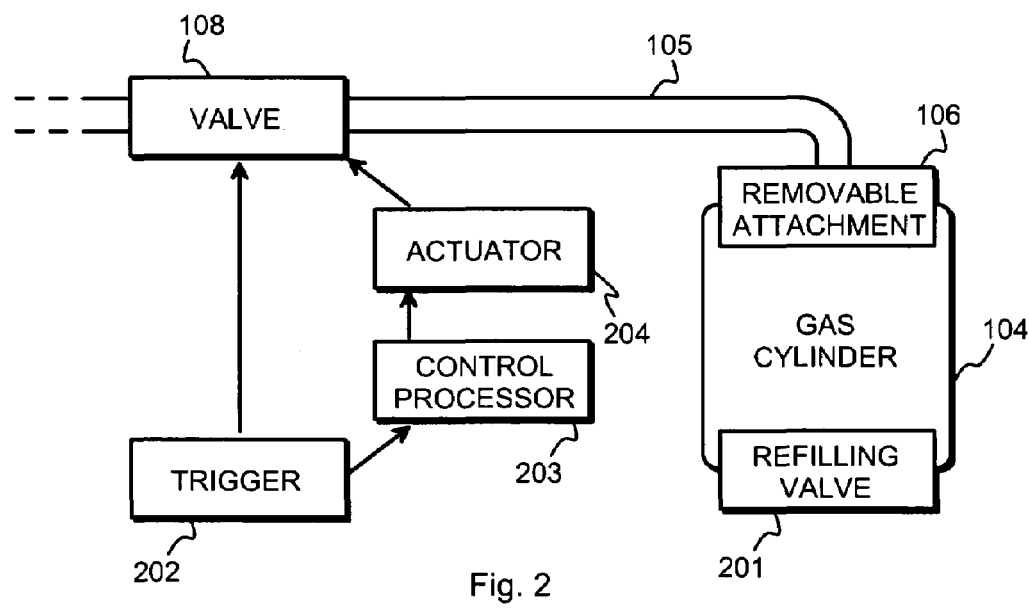
FIG. 2 illustrates some aspects of gas administration in a measurement apparatus according to an embodiment of the invention.

FIG. 2 illustrates some more detailed features of a gas administration subsystem for a measurement apparatus according to an embodiment of the invention. Some of the features illustrated in FIG. 2 are alternatives of each other. In order to make it easy to incorporate the administration of protective gas to a handheld, portable, or small table-sized measurement apparatus, it is advantageous to use a relatively small, replaceable gas cartridge as the gas cylinder 104. Replaceable gas cartridges of suitable kind are widely known e.g. from the technology of hand tools powered by pressurized gas, as well as from self-inflating buoyancy products. Using replaceable gas cartridges requires that the attachment means 106 are designed to facilitate easy removal of used gas cartridges and the attachment of fresh ones. Suitable attachment means are likewise known from the technical fields mentioned above as examples. Alternatives include providing the gas cylinder 104 with a refilling valve 201, so that it can be refilled with gas (also) without removing it from the measurement apparatus, or providing a connection from an external, standalone gas cylinder to the gas conduit 105.

As a part of the user interface of the measurement apparatus, there is most advantageously provided a trigger 202. Pressing or otherwise actuating the trigger 202 causes the controllable valve 108 to open, allowing gas to flow from the gas cylinder 104 through the gas conduit 105 to the sample area. Again, at least two alternative solutions exist. There may be a direct mechanical coupling from the trigger 202 to the controllable valve 108, or actuating the trigger 202 may give an input signal to a control processor 203, which is adapted to interpret this input signal as a command for opening the controllable valve 108. In the last-mentioned case the control processor 203, which in the block diagram of FIG. 1 is a part of the control subsystem 112, is adapted to command an actuator 204 to open the controllable valve 108.

In order not to use more gas than what is needed for a measurement, it is advantageous to somehow ensure that the controllable valve 108 only stays open for as long as the protective gas atmosphere is needed. This time may be as short as in the order of few seconds, because LIBS measurements take place relatively quickly. Mechanical means for regulating the amount of gas delivered in a single shot are known at least from the technology of inhalators used to administrate medical substances in gaseous form to patients. If a combination of a control processor 203 and an actuator 204 is used, it is very simple to program the control processor 203 so that it only tells the actuator 204 to keep the controllable valve 108 open for a predetermined duration of time or otherwise limits the amount of delivered gas.

Figure 3:
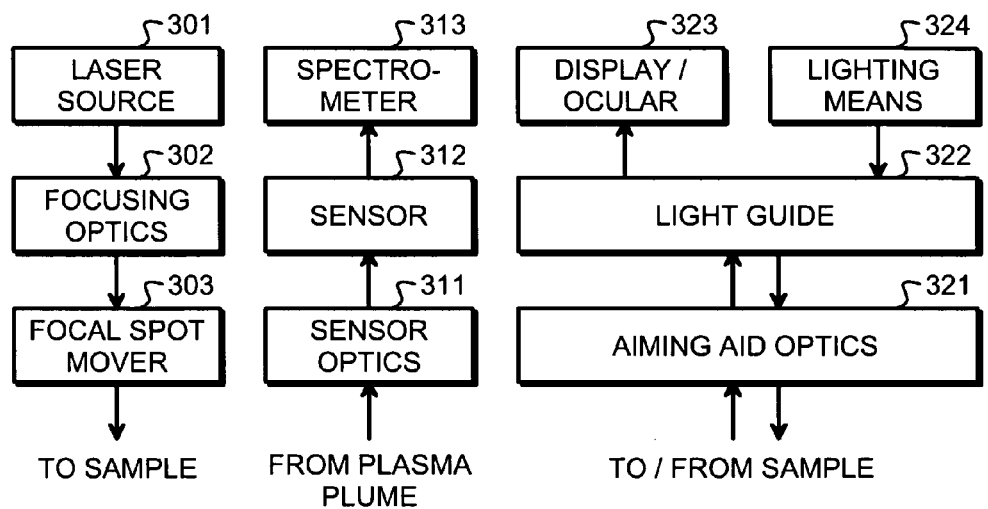
FIG. 3 illustrates parts of a LIBS subsystem in a measurement apparatus according to an embodiment of the invention.
Figure 4:
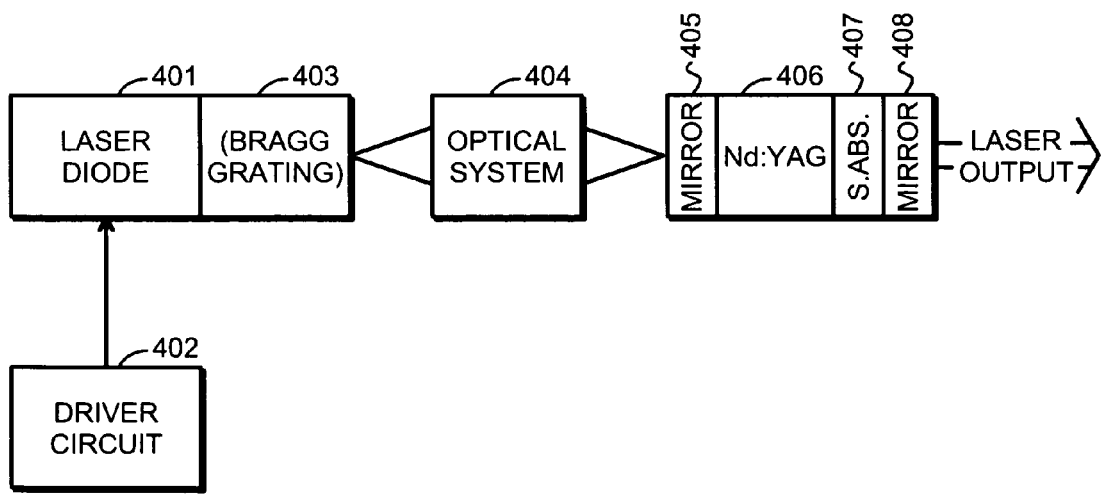
FIG. 4 illustrates parts of an exemplary laser source.

FIG. 3 illustrates certain aspects of an exemplary LIBS subsystem in a measurement apparatus according to an embodiment of the invention. There must be a laser source 301, which is capable of producing a momentary energy density at a focal spot which is high enough to change a small portion of the sample material into a state of plasma. One suitable laser source is illustrated in more detail in FIG. 4. The device is a so-called Nd:YAG microlaser and represents a class of passively Q-switched pulse lasers. A high-brightness laser diode 401 receives a carefully controlled driving current from a driver circuit 402. At the relatively small diode aperture of the laser diode 401 a so-called pump beam appears. The carrier wave power of the pump beam is typically in the order of a few watts.

A collimating and focusing optical system 404 concentrates the pump beam on an active medium 406, typically Nd:YAG (Neodymium (3+)-doped Yttrium Aluminum Garnet), which has a saturable absorber 407 attached to one end. The saturable absorber 407 may be for example a slab of $Cr^{4+}$:YAG (Chromium (4+)-doped Yttrium Aluminum Garnet). At the input face of the active medium 406 there appears a dichroic mirror 405 which has high reflectivity at the wavelength of the final laser output beam but good transmissivity at the wavelength of the pump beam. The output face of the Nd:YAG/Cr:YAG combination comprises a semitransparent mirror 408, which is semitransparent at the wavelength of the final laser output beam.

The output of the Nd:YAG microlaser consists of high-power pulses with pulse duration in the order of nanoseconds. Pulse repetition rate can be controllably varied from monopulse applications to the order of a few kHz. General characteristics of Nd:YAG microlasers are presented for example in the publication R. Dabu, A. Stratan, L. Neagu: "Design and characterization of an end-pumped Nd:YAG microlaser", Romanian Reports in Phisics, Vol. 56, No. 2, pp. 294-305, 2004, which is incorporated herein by reference.

The stability of the passively Q-switched pulse laser is highly dependent on the output stability of the pump laser. This is especially important in portable applications, where the ambient temperature can easily rise above +40 degrees centigrade. The stability of the output characteristics of laser diodes can be improved by equipping them with appropriately driven Peltier-elements adapted to produce a cooling effect, but this causes a large increase in the overall energy consumption of the apparatus because Peltier elements traditionally have only moderate efficiency. According to a specific embodiment of the present invention the stability problem can be solved by locking the output wavelength of the laser diode 401. In practice this is most easily accomplished by using a so-called fabry-perot filter 403 at the exit of the laser diode, which acts as a bandpass filter that only passes the desired wavelength(s). Fabry-perot filters, specifically ones based on fiber bragg gratings and suitable for this purpose are known e.g. from patent publications U.S. Pat. No. 5,048,913, U.S. Pat. No. 5,104,209 and U.S. Pat. No. 5,216,739.

Instead of a single laser source it is possible to use two or more laser sources producing laser light on different wavelengths, or a single laser source and one or more nonlinear optical crystals such as Potassium Titanyl Phosphate (KTP) crystals and appropriate timing, to vary the way in which the optical stimulus is provided to the sample. With frequency multipliers it is possible to change the initial infrared range wavelength of the plasma-inducing laser light to e.g. one half or one quarter of the original wavelength.

Referring back to FIG. 3, focusing optics 302 may include, in a way very well known as such, optical elements such as lenses, mirrors, slits, grids, collimators and the like. The task of the focusing optics 302 is to focus the output beam of the laser source 301 onto the surface of a sample. Relatively gentle changes in beam diameter, synonymous with relatively long focal length, are preferred because measurement apparatuses of the kind meant in the invention are frequently used in field conditions, where it is not possible to require very exact positioning of the sample in relation to the measurement head. A long focal length helps to reduce the effect of variations in measurement geometry. However, even if in this context the focal length can be said to be long if it allows an uncertainty of submillimeter scale in sample positioning, it should be understood that in a macroscopic scale (at distances larger than a few millimeters) and from the point of view of a user operating the measurement apparatus, the plasma-inducing laser diverges so quickly and has such a harmless wavelength that radiation hazards to the environment are negligible. Due to the expected difficulties in positioning the sample very exactly we may define that the focal spot is "on the surface of the sample" if it is close enough to the surface (in- or outside the sample material) to allow the formation of plasma.

According to an aspect of the invention there is provided a focal spot mover 303, the task of which is to move the focal spot of the plasma-inducing laser beam across the surface of a sample for a distance that is large compared with the diameter of the focal spot. The purpose of moving the focal spot is to cover a more representative portion of the sample material than what happens to be within the area of the focal spot. Additionally moving the focal spot prevents repeated laser pulses from eating away the surface of the sample material at one point. Although the size of the "drilling hole" created by a stationary focal spot would be so small that it would seldom be even visible, let alone cause any actual disadvantage, the drilling effect may involve other drawbacks for example in applications where the measurement is aimed at investigating the very surface of a sample the material composition of which varies as a function of depth.

Due to the very short duration of each single laser pulse, the movement of the focal spot during a single pulse is negligible and can be omitted. However, when pulses are repeated for a measurement duration in the order of a few seconds, even a relatively simple focal spot mover arrangement is capable of making the focal spot traverse a significant distance, in the order of one millimeter or a few millimeters. The physical implementation of the focal spot mover 303 may involve e.g. an electrically moved mirror or a rotating lens. The movement of the focal spot on the sample surface may be oscillatory, so that it travels e.g. a linerar track back and forth or along a circular or elliptical track. The electric power needed to operate the focal spot mover comes from the power subsystem of the measurement apparatus (see block 110 in FIG. 1) and the moving is accomplished under the control of the control subsystem (see block 112 in FIG. 1). It may be advisable to allow the user to have some online control over the way in which the focal spot is moved, especially if the sample to be investigated is so small or heterogeneous that moving the focal spot might involve the risk of making it wander out of the actual area of interest. Such control is most advantageously combined with the aiming aid discussed in more detail below.

Sensor optics 311 are provided for collecting optical emissions from a plasma plume induced at the focal spot and for directing the collected optical emissions to the optical sensor 312. In their simplest form the sensor optics 311 consist of a free passage of light between the sample surface and the sensor 312. More elaborate solutions may include for example lenses, mirrors, light guides and other optical elements. In order to keep reflected quanta of the incident laser radiation from interfering with the detection of optical emissions it is advantageous to use an infrared filter as a part of the sensor optics 311. A normal Nd:YAG microlaser produces incident radiation at the wavelength of about 1060 nm, which is in the infrared range, so it is effectively filtered out by an infrared filter.

The sensor 312 detects the optical emissions collected by the sensor optics 311. In order to provide meaningful results the sensor 312 must be sensitive to wavelength and intensity. However, these requirements are relatively easily filled. A line of photodiodes, similar to those used in regular barcode scanners, is often sufficient. The sensor 312 is coupled to a spectrometer 313, which is an electronic circuit adapted to read the detection results from the sensor 312 so that information about spectral distribution and intensity is preserved, and to integrate consecutive readings over a predetermined time. Together, the sensor 312 and the spectrometer 313 constitute an arrangement adapted to convert the collected optical emissions into an electronic signal representative of the spectral distribution and intensity of the optical emissions. If a focal point mover is used to move the focal spot of the plasma-inducing laser, the detection process must be adapted to take into account the corresponding changes in measurement geometry. This can be easily accomplished for example by using the movable mirror that causes the focal spot to move also as a part of the sensor optics 311.

According to an aspect of the invention, the measurement apparatus comprises an optical aiming aid adapted to provide the user with visual feedback about the location on the sample surface that will be subjected to measurement. An image of the appropriate part of the sample surface is conducted through aiming aid optics 321 and a light guide 322 to a display or ocular 323, which we will designate as the display device. In order to ensure sufficient lighting of the sample it is advisable to provide lighting means 324, from which light can be taken through the light guide 322 and aiming aid optics 321 to the target area on the sample surface.

According to a first alternative, the lighting means 324 produce a general background lighting in order to provide a sufficiently bright image of the target area on the sample surface to the display device. Other aiming means, such as frames and/or crosshairs, can then be used to indicate, exactly which point on the sample surface the laser beam from the laser source 301 will hit.

According to another alternative, the lighting means 324 may comprise another laser source, which in contrast to the plasma-inducing laser source 301 is adapted to produce a laser beam in the visible wavelength range. This visible laser beam can be focused through the light guide 322 and the aiming aid optics 321 onto the sample surface, where its reflection constitutes a visible indicator spot that shows, which point on the sample surface the laser beam from the laser source 301 will hit. In order to keep the indicator laser from interfering with the optical measurement it is advisable to make its operation controllable so that it will be shut off during the optical measurement. Alternatively filtering arrangements can be utilized.

The light guide 322, the aiming aid optics 321, the focusing optics 302 and the focal spot mover 303 may include shared components. For example, also the visible laser beam originating from the lighting means 324 may be directed through the focal spot mover 303 in order to move the indicator spot on the sample surface in a manner that is similar to the movement of the focal spot of the plasma-inducing laser beam. This way the user can easily check, in the case of a very small or very heterogeneous sample, that the movement of the focal spot will not take it outside the area of interest. If the movement caused by the focal spot mover 303 is controllable, the user may first check it by using the indicator spot and by changing e.g. the extent or direction of linear movement or the radius of a circular movement so that only an appropriate target area of the sample surface will be covered by the movement of the focal spot. Controlling the movement caused by the focal spot mover 303 necessitates movement-controlling input means in the user interface of the measurement apparatus, as well as a coupling from these to a part of the control subsystem that actually controls the focal spot mover 303.

Figure 5:
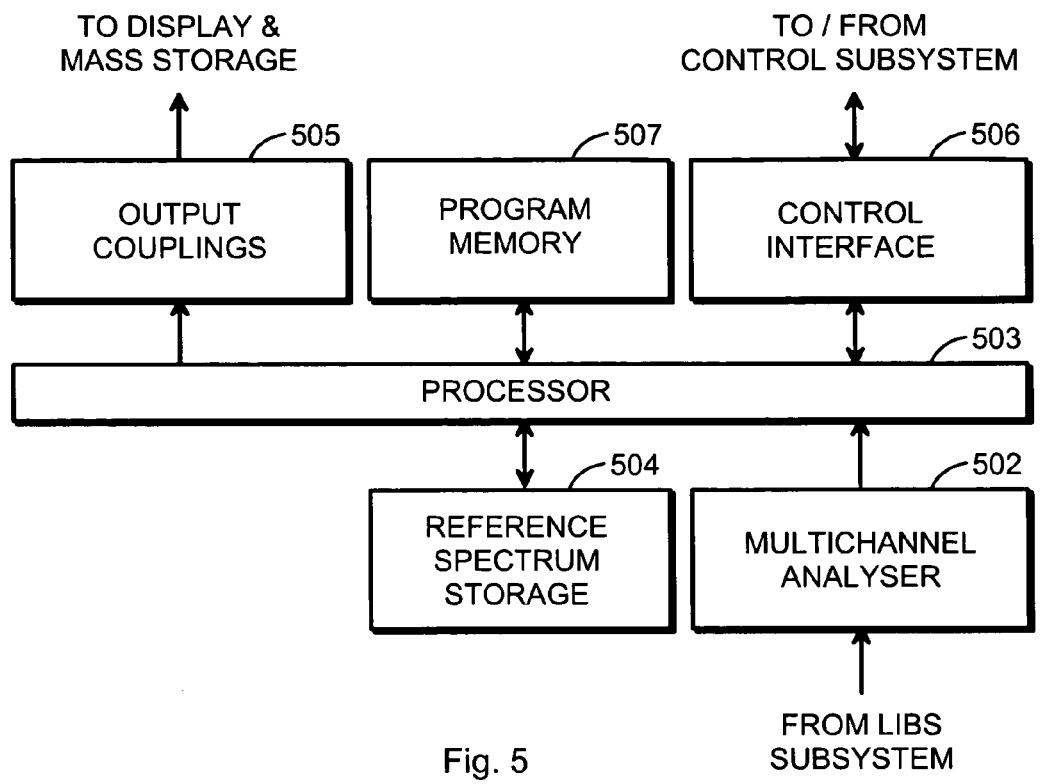
FIG. 5 illustrates an exemplary processing subsystem in an apparatus according to an embodiment of the invention.

FIG. 5 illustrates schematically parts of an exemplary processing subsystem. A multichannel analyzer 502 collects the output information from the LIBS subsystem into an optical spectrum. A processor 503 is adapted to compare the measured spectra with reference information stored in a reference spectrum storage 504. Output information is taken through output couplings 505 to e.g. a display and/or a mass storage. A control interface 506 is provided to link the processing subsystem to the control subsystem. The programs executed by the processor 503 are stored in a program memory 507.

The control subsystem of a measurement apparatus according to the invention is essentially a processor or a corresponding programmable device, adapted to exchange commands, instructions and other information with other parts of the apparatus and to execute programmed instructions for controlling the operation of the apparatus. The division into a control subsystem and a processing subsystem may be somewhat blurred, because they can both be built around the same processor.

Figure 6:
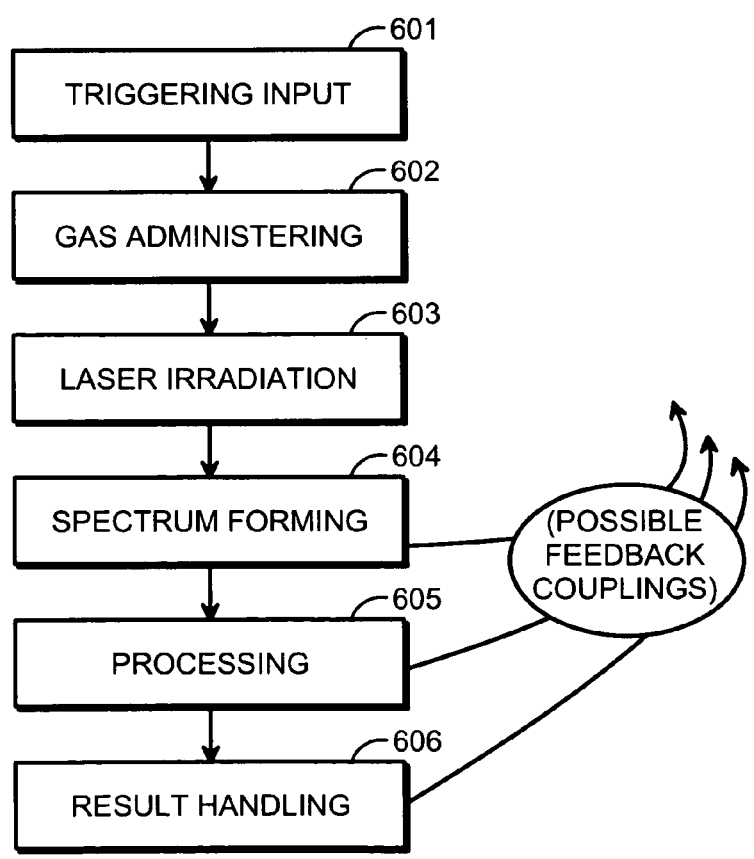
FIG. 6 illustrates aspects of a method according to an embodiment of the invention.

FIG. 6 illustrates some method aspects of the invention. A measurement begins when a triggering input is received at step 601. Typically a user pulls a measurement trigger or otherwise performs an action that gives the measurement apparatus a signal to start measuring. If an aiming aid is used, illuminating an area of the sample surface and displaying an image of at least a part of the illuminated area to a user may be thought to be incorporated in step 601.

Gas is administrated to the target area at step 602, preferably (but not mandatorily) before irradiation with the plasma-inducing laser begins at step 603. Exposure times in LIBS are typically much shorter than for example in XRF: for an analysis that requires 60-120 seconds of X-ray exposure and fluorescence detection an optical exposure time of only few seconds may be sufficient.

Spectra are collected at step 604, results are processed at step 605 and the processed results are directed to display and/or mass storage at the results handling step 606. From one or more of steps 604, 605 and 606 there may be feedback couplings to the previous steps of the method. For example, it is possible to keep the irradiation of step 603 active until an indication from results processing tells that enough optical emissions have been received, after which the laser source is shut off.

The LIBS analysis of a target may take place in stages, without moving the focal spot, so that each stage gives information about a layer of the sample which was reached in "drilling" a hole to the sample with the plasma-inducing layer. In FIG. 6 that could involve going through the steps 601-606 a number of times, so that each stage is initiated by the user separately. Another alternative is to program the measurement apparatus so that if during a measurement the obtained spectrum has first followed a first pattern but thereafter begins to change from that first pattern more than some predefined criteria allow, the first pattern is stored as the characteristic spectrum of a first layer and a new measurement stage is automatically commenced. A yet another alternative is to perform the measurement regularly in stages, for example allowing a fixed number of plasma-inducing laser pulses to hit the sample during each stage, and storing the spectra from the repetitive measurement stages as a time series that illustrates, how the measurement results change from stage to stage.

The invention claimed is:

1. An arrangement for non-destructively analyzing the composition of a delicate sample, comprising:
a laser source adapted to produce a pulsed laser beam,
focusing optics adapted to focus said pulsed laser beam into a focal spot on the sample, a value of which depends at least partly on absence of visual defects, wherein said focusing optics is configured to direct said focal spot on such surface of the sample on which a visual defect would deteriorate the value of the sample,
a sensor adapted to receive and detect optical emissions from particles of the sample excited by said pulsed laser beam and
a processing subsystem adapted to produce information of the composition of the sample based on the optical emissions detected by said sensor.

2. An arrangement according to claim 1, comprising a gas administration subsystem adapted to controllably deliver gas to a space around said focal spot.

3. An arrangement according to claim 2, comprising:
a gas conduit,
attachment means for attaching a gas cylinder to one end of said gas conduit,
a nozzle at another end of said gas conduit, said nozzle being directed towards said space around said focal spot and
a controllable valve along said gas conduit, said controllable valve being adapted to open and close said gas conduit as a response to user action.

4. An arrangement according to claim 3, comprising a trigger and a mechanical coupling between said trigger and said controllable valve.

5. An arrangement according to claim 3, comprising a trigger, a control processor adapted to receive an input signal from said trigger, and an actuator adapted to receive a command from said control processor as a response to an input signal from said trigger to said control processor and adapted to open said controllable valve as a response to said command.

6. An arrangement according to claim 3, wherein said attachment means are adapted to removably receive a replaceable gas cartridge.

7. An arrangement according to claim 6, comprising an outer cover adapted to at least partly enclose a replaceable gas cartridge attached to said attachment means.

8. An arrangement according to claim 3, comprising a gas cylinder attached to said attachment means and a refilling valve for refilling said gas cylinder.

9. An arrangement according to claim 1, comprising a focal spot mover adapted to move said focal spot on a surface of said sample during a measurement.

10. An arrangement according to claim 9, wherein said focal spot mover comprises a movable mirror.

11. An arrangement according to claim 1, wherein said laser source is a passively Q-switched pulse laser comprising a laser diode, an active medium and a saturable absorber.

12. An arrangement according to claim 11, comprising a fabry-perot filter between said laser diode and said active medium for locking the output wavelength of said laser diode.

13. An arrangement according to claim 11, comprising an infrared filter between said space around said focal spot and said optical sensor, for keeping reflections of said laser beam from interfering with the detection of optical emissions.

14. An arrangement according to claim 1, comprising an optical aiming aid adapted to provide a user with visual feedback about the location of said focal spot on said surface of said sample.

15. An arrangement according to claim 14, wherein said optical aiming aid comprises:
a display device and
aiming aid optics and a light guide adapted to conduct an image of a part of the sample surface to said display device.

16. An arrangement according to claim 15, comprising aiming means adapted to indicate on said display device at which point on the sample surface the focal spot will be.

17. An arrangement according to claim 15, comprising a source of laser light of visible wavelength adapted to illuminate a spot on said surface of said sample, said illuminated spot being coincident with said focal spot.

18. A method for non-destructively analyzing the composition of a delicate sample, comprising:
producing a pulsed laser beam and focusing said pulsed laser beam into a focal spot on a surface of said sample, a value of which depends at least partly on absence of visual defects, wherein said focusing optics is configured to direct said focal spot on such surface of the sample on which a visual defect would deteriorate the value of the sample,
detecting optical emissions coming from particles of said sample upon said sample being exposed to said pulsed laser beam at said focal spot and
determining the material composition of said sample based on the detected optical emissions.

19. A method according to claim 18, comprising controllably delivering gas to a space around said focal spot.

20. A method according to claim 18, comprising moving said focal spot across said surface of said sample during the detection of optical emissions.

21. A method according to claim 18, comprising illuminating an area of said surface of said sample and displaying an image of at least a part of the illuminated area to a user.

22. A method according to claim 21, comprising directing a laser beam of visible wavelength to a location on said surface of said sample coincident with the location of said focal spot.

23. A method for non-destructively analyzing the composition of a delicate sample, a value of which depends at least partly on absence of visual defects, comprising:
producing a pulsed laser beam and focusing said pulsed laser beam into a focal spot on a surface of said sample,
detecting optical emissions comma from particles of said sample upon said sample being exposed to said pulsed laser beam at said focal spot and
determining the material composition of said sample based on the detected optical emissions comprising optically drilling a deepening hole into the surface of said sample by allowing repetitive pulses of said pulsed laser beam to hit the sample at a constant location, and repetitively detecting optical emissions coming from particles of said sample upon said sample being exposed to said pulsed laser beam at said focal spot, for determining the material composition of said sample at a plurality of depths below the surface of the sample.

* * * * *